US010709545B2

(12) United States Patent
Schuessler et al.

(10) Patent No.: US 10,709,545 B2
(45) Date of Patent: Jul. 14, 2020

(54) IMPLANTABLE PROSTHESES FOR TISSUE EXPANSION

(71) Applicant: Allergan, Inc., Irvine, CA (US)

(72) Inventors: David J. Schuessler, Santa Ana, CA (US); Steven A. Schultz, Coto de Caza, CA (US)

(73) Assignee: Allergan, Inc., Irvine, CA (US)

(*) Notice: Subject to any disclaimer, the term of this patent is extended or adjusted under 35 U.S.C. 154(b) by 115 days.

(21) Appl. No.: 15/937,762

(22) Filed: Mar. 27, 2018

(65) Prior Publication Data

US 2018/0280131 A1  Oct. 4, 2018

Related U.S. Application Data

(60) Provisional application No. 62/477,252, filed on Mar. 27, 2017.

(51) Int. Cl.
*A61F 2/12* (2006.01)
*A61L 27/50* (2006.01)
(Continued)

(52) U.S. Cl.
CPC ............... *A61F 2/12* (2013.01); *A61L 27/18* (2013.01); *A61L 27/44* (2013.01); *A61L 27/48* (2013.01); *A61L 27/50* (2013.01); *A61B 90/02* (2016.02); *A61F 2250/0003* (2013.01); *A61L 2430/04* (2013.01)

(58) Field of Classification Search
CPC ...... A61F 2/12; A61F 2/52; A61F 2210/0061; A61L 27/56; A61L 27/18; A61K 9/70; A61K 9/0004; A61B 90/02
See application file for complete search history.

(56) References Cited

U.S. PATENT DOCUMENTS 4,157,085 A   6/1979  Austad
4,467,806 A * 8/1984  Bhiwandiwala ...... A61M 29/02
                                              606/193
(Continued)

FOREIGN PATENT DOCUMENTS

EP       1559685     8/2005
WO   WO 2010/022130   2/2010

OTHER PUBLICATIONS

International Search Report and Written Opinion from PCT/US2018/024596, dated Jul. 4, 2018, 11 pages.

*Primary Examiner* — Brian A Dukert
*Assistant Examiner* — Rebecca Lynee Zimmerman
(74) *Attorney, Agent, or Firm* — Nathan S. Smith; Sujohn Das; Morgan, Lewis & Bockius LLP (57) ABSTRACT

A device can be used for both tissue expansion within a body of a patient as well as a permanently implanted prosthesis. Such a device can include an expandable elastomeric matrix and granules of a solute embedded within the matrix. The matrix can define boundaries of a plurality of chambers within the matrix. The device, when implanted within the body of the patient, can be exposed to fluid within the patient to create an osmotic gradient across a boundary of the device. Based on the gradient, fluid permeates the elastomer and gradually expands the chambers. The rate of expansion can be programmed to allow the body to naturally adapt to the volume, which increases until achieving a target volume in an expanded state.

18 Claims, 4 Drawing Sheets

(51) Int. Cl.
*A61L 27/48* (2006.01)
*A61L 27/18* (2006.01)
*A61L 27/44* (2006.01)
*A61B 90/00* (2016.01)

(56) References Cited

U.S. PATENT DOCUMENTS

| | | | | |
|---|---|---|---|---|
| 5,005,591 A | * | 4/1991 | Austad | A61B 90/02 |
| | | | | 128/899 |
| 2009/0254179 A1 | * | 10/2009 | Burnett | A61B 5/076 |
| | | | | 623/8 |
| 2015/0351900 A1 | | 12/2015 | Glicksman | |

* cited by examiner

IMPLANTABLE PROSTHESES FOR TISSUE EXPANSION

CROSS-REFERENCE TO RELATED APPLICATIONS

The present application claims the benefit of U.S. Provisional Application No. 62/477,252, filed Mar. 27, 2017, the entirety of which is incorporated herein by reference.

BACKGROUND

Field

The present disclosure relates to prosthetic implants and, more particularly, to breast implants and tissue expanders.

Description of the Related Art

Implantable prostheses are commonly used to replace or augment body tissue. In the case of breast cancer, a mastectomy is sometimes necessary to remove some or all of the mammary gland and surrounding tissue, which creates a void. This void may be filled with a fluid-filled implantable prosthesis. The implant serves to support surrounding tissue and to maintain the appearance of the body. The restoration of the normal appearance of the body has an extremely beneficial psychological effect on post-operative patients, alleviating much of the shock and depression that often follows extensive surgical procedures.

Soft implantable prostheses typically include a relatively thin and quite flexible envelope or shell made of silicone elastomer. The shell is filled either with a silicone gel or with a physiologic saline solution. The filling of the shell may take place before or after the shell is implanted in the patient.

A saline-filled implant includes an outer shell of several layers of silicone elastomer having a valve or fill port on one side. The prosthesis is typically implanted into the breast cavity in an empty or only partially filled state. The implant is then inflated to its final size by means of the valve or fill port. This helps reduce the size of the needed incision, and enables a surgeon to adjust and even microadjust the volume of the implant.

In breast reconstruction, prior to implantation of a long-term prosthesis, it is common practice to utilize a more temporary implant, for example, what is known as a "tissue expander" in order to gradually create the space necessary for the long-term prosthesis. For example, in some situations, such as a mastectomy, the chest tissues may be flat and tight, and an expander can serve to prepare the body for receiving a long-term prosthesis. Tissue expanders can also be used in other places in the body to expand healthy tissue to replace a nearby defect such as a burn or scar. Essentially, a tissue expander comprises an inflatable body, having an inflation valve connected thereto. The valve may be formed into the inflatable body itself or may be remotely located and connected to the inflatable body by means of an elongated conduit.

The inflatable body of the tissue expander is placed subcutaneously in the patient, at the location of where tissue is to be expanded. The inflation valve, whether on the implant or remote thereto, is also subcutaneously positioned or implanted, and is configured to allow gradual introduction of fluid, typically saline, into the inflation body, by injection with a syringe. After gradual inflation at pre-determined intervals, the skin and subcutaneous tissues overlying the expander are consequently caused to expand in response to the pressure exerted upon such tissues by the inflatable body as solution is gradually introduced therein.

After gradual inflation at pre-determined intervals, which may extend over weeks or months, the skin and subcutaneous tissue will expand to the point where further medical procedures can be performed, such as the implantation of a long-term prosthesis, plastic and reconstructive surgery, or for use of the skin and subcutaneous tissue for use in some other part of the body.

SUMMARY

An implantable device in accordance with embodiments of the present disclosure can provide slow and continuous expansion of the tissue with a very small amount of tissue growth each day without any external influence after initial implant. Rather than requiring an additional operation to remove the expander and replace it with a long-term implant, tissue expanders in accordance with embodiments of the present disclosure can be left in place as the long-term implant.

An implantable device in accordance with embodiments of the present disclosure can address safety concerns relating to inadvertent release of high concentrations of salt or other solutes leading to necrosis and other damage to tissues upon pre-mature rupture of a tissue expander. The implantable device can expand and be supported without reliance on certain substances such as hydrogels, which are subject to chemical inconsistencies, degradation, and poor performance in tissue expansion. The implantable device can also operate without a complicated design that requires active intervention for serial inflations.

An implantable device in accordance with embodiments of the present disclosure can be used for both tissue expansion within a body of a patient as well as a long-term implanted prosthesis. The implantable device can include an expandable elastomeric matrix and granules of a solute embedded within the matrix.

The matrix of an implantable device can define boundaries of a plurality of chambers within the matrix. The device, when implanted within the body of the patient, can be exposed to fluid within the patient to create an osmotic gradient across a boundary of the device. For example, the boundaries can be permeable to water at body temperatures, such as a temperature of between 35° C. and 41° C. Based on the gradient, fluid permeates the elastomer and gradually expands the chambers. The rate of expansion can be programmed to allow the body to naturally adapt to the volume, which increases until achieving a target volume in an expanded state. The implantable device can include a shell extending about a periphery of the matrix to enclose the matrix therewithin.

Additional features and advantages of the subject technology will be set forth in the description below, and in part will be apparent from the description, or may be learned by practice of the subject technology. The advantages of the subject technology will be realized and attained by the structure particularly pointed out in the written description and claims hereof as well as the appended drawings.

It is to be understood that both the foregoing general description and the following detailed description are exemplary and explanatory and are intended to provide further explanation of the subject technology as claimed.

BRIEF DESCRIPTION OF THE DRAWINGS

The accompanying drawings, which are included to provide further understanding of the subject technology and are

DETAILED DESCRIPTION

In the following detailed description, specific details are set forth to provide an understanding of the subject technology. It will be apparent, however, to one ordinarily skilled in the art that the subject technology may be practiced without some of these specific details. In other instances, well-known structures and techniques have not been shown in detail so as not to obscure the subject technology.

As described above, tissue expanders can be used to produce additional native tissue for skin and soft tissue defects and for breast reconstruction. A typical tissue expander can include a balloon-like device that is implanted within or next to the area needing the additional tissue. The tissue expander can be gradually filled with a solution (e.g., saline), typically with serial, periodic inflations with percutaneous needle injections through a port of the tissue expander.

This serial expansion process requires the patient to visit the healthcare provider multiple times to provide the inflations over the course of the treatment. The patient must endure the needle injection procedure. The injection ports can be difficult to locate, and they can malfunction and leak the fluid contained therein. Each injection procedure to inflate the tissue expander introduces a risk of infection. Some tissue expander injection ports include a magnet to facilitate location thereof, but the magnet can create a contraindication during an MRI procedure. Additionally, each inflation introduces a bolus of fluid, which can cause discomfort and pain and potentially damage the surrounding tissue due to the increased pressure from the sudden expansion of the balloon. After the expansion process, the tissue expander is typically removed and replaced with a permanent breast implant.

In contrast, tissue expanders in accordance with embodiments of the present disclosure can provide slow and continuous expansion of the tissue with a very small amount of tissue growth each day without any external influence after initial implant. Rather than requiring an additional operation to remove the expander and replace it with a permanent implant, tissue expanders in accordance with embodiments of the present disclosure can be left in place as the permanent implant.

Furthermore, tissue expanders in accordance with embodiments of the present disclosure can address safety concerns relating to inadvertent release of high concentrations of salt or other solutes leading to necrosis and other damage to tissues upon pre-mature rupture of a tissue expander. Tissue expanders in accordance with embodiments of the present disclosure can expand and be supported without reliance on certain substances such as hydrogels, which are subject to chemical inconsistencies, degradation, and poor performance in tissue expansion. Tissue expanders in accordance with embodiments of the present disclosure can also operate without a complicated design that requires active intervention for serial inflations.

According to some embodiments of the present disclosure, a prosthetic implant can serve as a tissue expander that produces controlled auto-inflation within the body for the gradual expansion of soft tissues, for example in breast reconstruction. The most common type of soft prosthesis shown for illustration purposes is for breast reconstruction or augmentation, though prostheses formed in accordance with the teachings herein may be used to restore or augment the appearance of soft tissue in the buttocks, chin, calf, etc.

Figure 1:
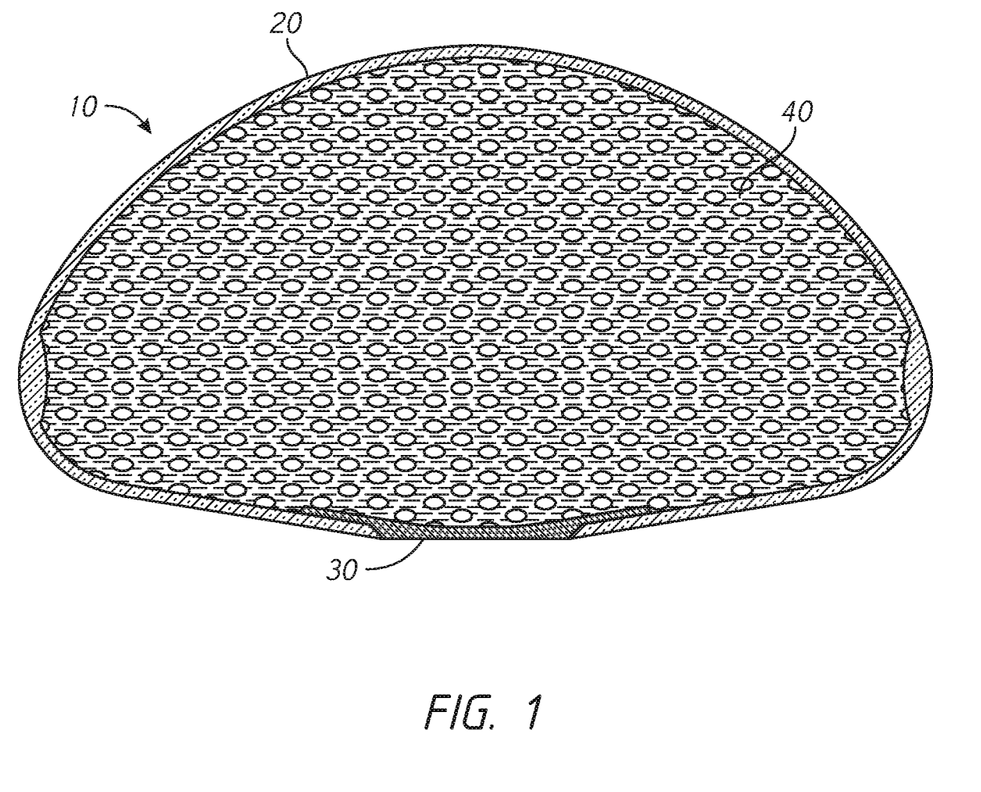
FIG. 1 illustrates a cross-sectional view through a prosthetic implant having a matrix and a shell, according to some embodiments of the present disclosure.

FIG. 1 illustrates an exemplary device 10 having a flexible outer shell 20 and a matrix 40 filling an internal cavity of the shell 20. In the embodiment shown in FIG. 1, an access valve 30 is provided on a side of the shell 20. The access valve 30 can provide controllable flow into or out of the shell 20. The access valve 30 can be self-sealing and actuated by a tool.

According to some embodiments, the shell 20 can be soft and flexible and encloses the matrix 40 for containing a fluid (e.g., saline). The shell 20 and/or the matrix 40 can include a semi-permeable membrane that selectively allows diffusion of certain substances across the semi-permeable membrane. For example, in the presence of an osmotic gradient, fluid can be driven from the body into the device 10 resulting in expansion thereof. In some embodiments, the semi-permeable membrane is permeable to water, but is not permeable to a solute. In some embodiments, the semi-permeable membrane is permeable to water, but is not permeable to an ionic solute selected from the group consisting of sodium, potassium, calcium, chloride, iodide, bromide, carbonate, bicarbonate, sulfate, sulfite, phosphate, acetate, and combinations thereof. In some embodiments, the semi-permeable membrane is permeable to water, but is not permeable to a water-soluble organic species. Water-soluble organic species include, but are not limited to amino acids, conjugate bases of amino acids, carboxylic acids, conjugate bases of carboxylic acids, (e.g. pyruvate, succinate, etc.), alcohols comprising 2 or more carbon atoms, monomeric and dimeric sugars, and peptides.

Figure 2:
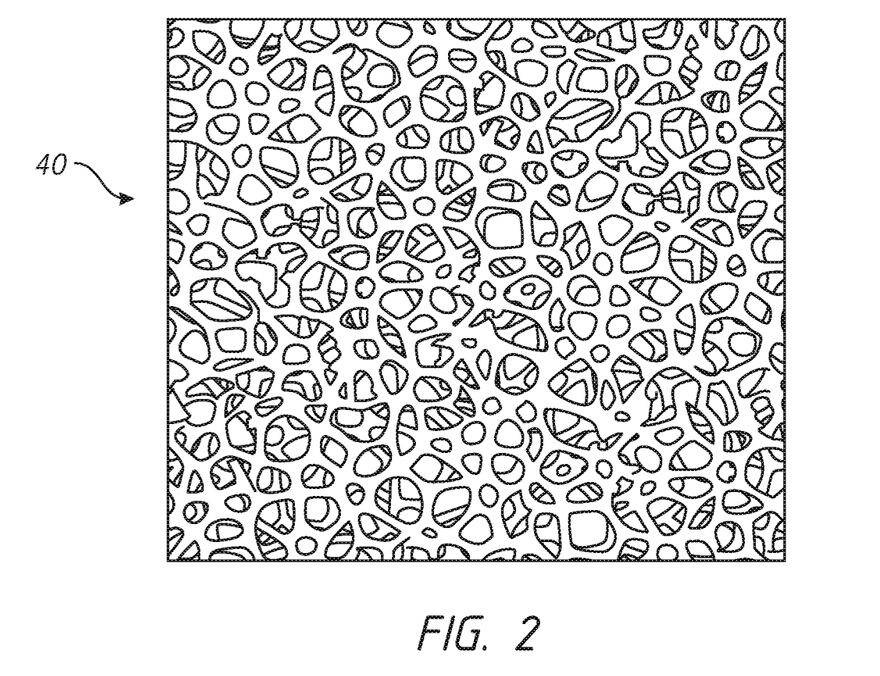
FIG. 2 illustrates a cross-sectional view through the matrix of FIG. 1, according to some embodiments of the present disclosure.
Figure 3:
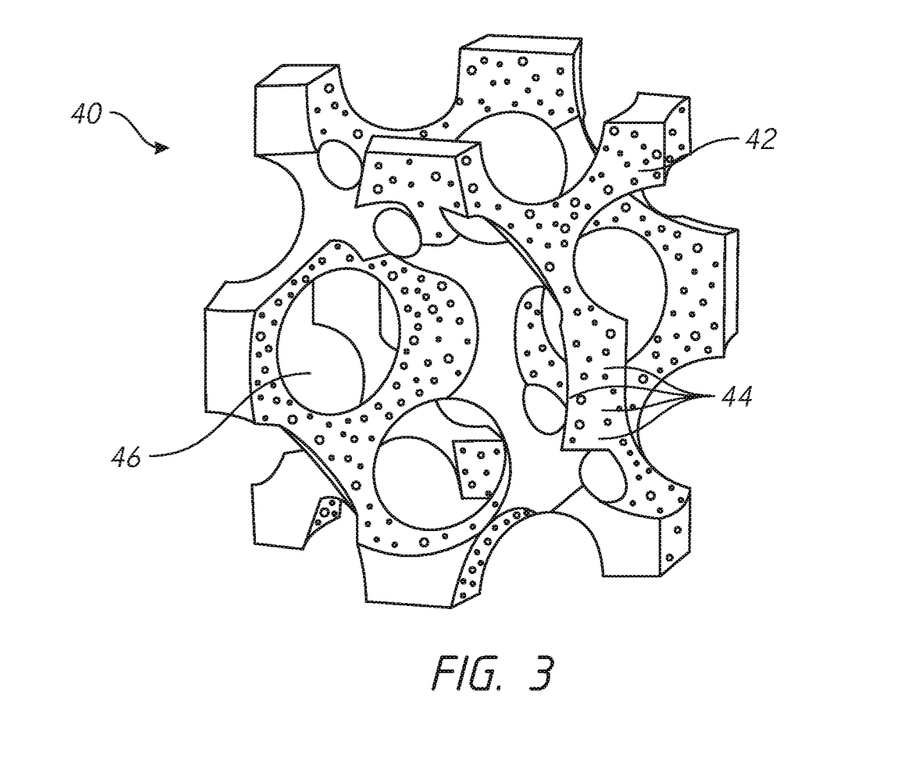
FIG. 3 illustrates a cross-sectional view through the matrix of FIG. 1, according to some embodiments of the present disclosure.

According to some embodiments, the matrix 40 of the device 10 can include walls 42 that define boundaries of multiple independent chambers 46 that are distributed throughout the matrix 40. For example, as illustrated in FIGS. 2 and 3, multiple chambers 46 can be interconnected in an open cell configuration. Each chamber 46 can be in fluid communication with other chambers 46 as the walls 42 partially separate adjacent chambers 46. The walls 42 can include or be constructed of an elastomer or other flexible material that is a semi-permeable membrane that selectively allows diffusion of certain substances. According to some embodiments, the matrix 40 can be a foam matrix.

According to some embodiments, the matrix 40 can include granules of a solute 44 embedded within cells in the elastomer of the walls 42. At least some of the granules of solute 44 can be fully encapsulated within the walls 42. Because the walls 42 are semipermeable, the presence of the granules of solute 44 can establish an osmotic gradient when in an aqueous environment and with respect to fluid within the chambers 46 and/or fluid outside of the device 10. The cells with the solute 44 in the walls 42 can selectively allow diffusion of certain substances, such as saline or body fluids, into the chambers 46 and toward the granules of solute 44. As the fluid diffuses through the walls 42, the cells containing the granules of solute 44 can absorb the fluid and cause the cells to expand which fill the chambers 46 and cause the matrix 40 to expand from the collapsed state to an uncollapsed or expanded state. According to some embodiments, expansion can continue until the device 10 reaches osmotic equilibrium with the external environment or until another constraint is applied.

The matrix 40 can be produced in specific shapes, as further discussed herein. By controlling the shape and material properties of the matrix 40 as well as the granule size and concentration of the solute 44, the expansion rate and expanded shape of the structure can be defined and controlled. This control of the expansion rate and the shape of the expanding structure can ultimately result in forming a permanent implant having a desired shape and size. The desired shape and size of the permanent implant will vary depending on the patient and tissue area being treated. For example, a higher concentration of the solute 44 can help establish a steeper slope for the osmotic gradient, thereby inducing more rapid diffusion and expansion of the device 10. A solution comprising solutes therein can be characterized as having an "osmotic concentration" or "osmolarity," which is defined as the total number of solute particles per liter of solution. By further example, the permeability of the walls 42 and/or the shell 20 can alter the rate of diffusion, thereby governing the rate of expansion as fluid flows into the device 10. Where the device 10 is allowed to expand until reaching osmotic equilibrium with the external environment, the concentration of the solute 44 can also govern how much fluid is required to reach osmotic equilibrium, thereby governing characteristics, such as volume, size, and shape, of the device 10 in the expanded state. For example, the amount and concentration of the solute within the device prior to expansion can be preselected based upon a measured solute concentration of the external environment. In the expanded state of device 10, diffused water will have increased the volume of the expanded device 10 and diluted the concentration of solute within device 10. The initial concentration and amount of solute in device 10 prior to expansion can be preselected in order to achieve a final diluted concentration that is equal to or in slight excess of a solute concentration of the external environment. For example, the final solute concentration (osmolarity) in the expanded state can be about 0%, about 0% to about 10%, about 5% to about 15%, about 10% to about 20%, or about 15% to about 25% greater than the total solute concentration (osmolarity) of the external environment.

According to some embodiments, the shell 20 and/or the matrix 40 can include a fluid permeation profile that characterizes the manner and conditions for allowing diffusion of materials therethrough. According to some embodiments, the shell 20 and/or the matrix 40 include a fluid permeation profile whereby fluid permeation occurs while within the body of the patient. The fluid permeation profile of the shell 20 and the matrix 40 can be the same or different. For example, the fluid permeation can occur at temperatures between about 35° C. and about 41° C., such as between about 36.5° C. and about 37.5° C. The fluid permeation profile of the shell 20 and/or matrix 40 can be controlled, for example, by configuration of the material composition of the shell 20 and/or matrix 40. For example, the material composition of shell 20 and/or matrix 40 can be configured with respect to characteristics including, hydrophilicity/hydrophobicity, porosity and pore size, elastic modulus, thickness, surface area, and concentration and amount of solute 44 encapsulated within matrix 40. Accordingly, the device 10 is designed to expand within the body of the patient at a rate of expansion that continues until reaching a target state, as described further herein.

Where the granules of solute 44 are encapsulated within the walls 42, any localized breach of the matrix 40 would only expose the surrounding environment to limited and tolerable releases of the solute 44. Although fluid within the chambers 46 could be released after such a breach, the encapsulated granules would remain within the walls 42, which are permeable to water, but impermeable to the solute 44. As such, the body into which the device 10 is implanted would not be exposed to high volumes of concentrated solutions. For example, conventional tissue expanders can include a saline solution which has a concentration of about 145-180 mEq/L, however because the solute 44 is encapsulated within the walls 42, exposure of tissues external to the device in the event of a localized breach would be significantly attenuated.

According to some embodiments, the device 10 can optionally include the shell 20 enclosing the matrix 40. The shell 20 can contribute to the shape of the device 10 in the expanded state. For example, the shell 20 can set a limit on the expansion of the matrix 40 by constraining the matrix 40 from expanding beyond the boundaries of the shell 20. The shell 20 can limit the expansion of the matrix 40 before the device 10 reaches osmotic equilibrium with its environment. The shell 20 can include a material having a high modulus of elasticity, such that the shell 20 includes a highly flexible, but not highly stretchable, material. According to some embodiments, the shell 20 can include reinforcing fibers, for example a polyester mesh, within its enclosed space to increase the resilience of the shell 20. According to some embodiments, the shell 20 can include portions having variable expansion characteristics to achieve non-uniformly distributed expansion. For example, the shell 20 can include a non-expandable or less expandable posterior portion to provide directional expansion anteriorally in the direction of an expandable or more expandable anterior portion. Expansion characteristics of the distinct portion governing the expansion can include, but are not limited to, thickness, modulus, texture, and material selection. The shell 20 may be made by dip-forming, spray-forming, etc. The exterior may be smooth or textured.

According to some embodiments, the device 10 can include either a smooth or textured outer surface. The device 10 can be circular, oval, crescent-shaped or other suitable shapes. The device 10, or portions thereof, can be formed of silicone rubber, a laminate of various forms of silicone, silicone copolymers, polyurethane, and various other elastomers in various combinations. In some embodiments, the elastomer component comprises a biocompatible, silicone elastomer material that is conventionally used in the construction of flexible shells for inflatable implants. For example, the elastomer component may comprise any suitable silicone elastomeric material. Suitable silicone elastomers include, but are not limited to, homopolymers such as polydimethylsiloxane or polymethylvinylsiloxane, or copolymers such as copolymers of diphenylsiloxane and dimethylsiloxane. The silicone elastomer can be cured by conventional means, for example, by using a polysiloxane crosslinker containing silicone-bonded hydrogen atoms with a vinyl containing siloxane elastomer and a platinum catalyst.

According to some embodiments, the matrix 40 can be a single monolith that is integrally formed by a network of walls 42. The monolithic structure can be contained within the shell 20.

Figure 4:
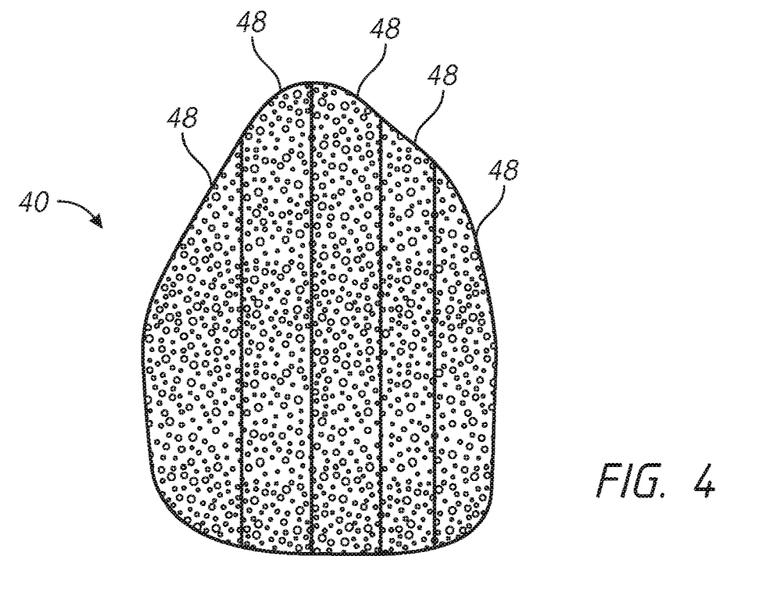
FIG. 4 illustrates a top view of a matrix having segments, according to some embodiments of the present disclosure.
Figure 5:
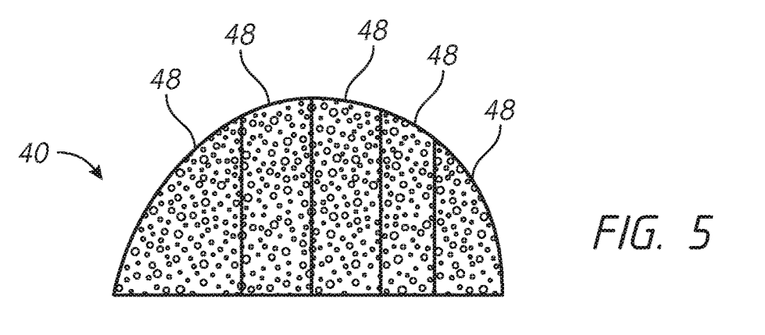
FIG. 5 illustrates a front view of the matrix of FIG. 4, according to some embodiments of the present disclosure.
Figure 6:
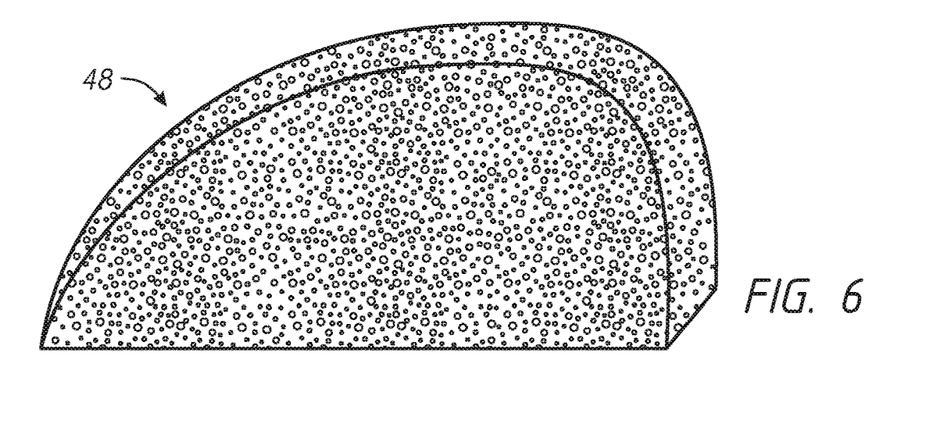
FIG. 6 illustrates a side view of a matrix segment, according to some embodiments of the present disclosure.

According to some embodiments, the matrix 40 can include a plurality of separate, distinct segments 48 that are each smaller than the whole matrix 40. The segments 48 can facilitate manipulation of the matrix 40, including placement and extraction, through arrangement of the individual segments 48. For example, as illustrated in FIGS. 4-6, the matrix 40 can have a composite shape that is defined by the arrangement of individual segments 48. The composite shape can be achieved while the segments 48 are arranged within the shell 20. The segments 48 can be formed by a series of cuts or partitions into the matrix 40 after formation of the matrix 40 as a monolithic structure. The cuts can be along intersecting or non-intersecting planes. For example, as illustrated in FIGS. 4 and 5, the segments can extend longitudinally and be divided along parallel planes. By further example, the segments can be divided along planes that intersect each other. Additionally, two or more of the segments can have different osmotic gradient properties, such as solute concentration, which would allow for different rates of expansion of the segments within the device.

The device 10 can be prepared for implant in a manner that facilitates the tissue expansion described herein. According to some embodiments, the solute 44 can be provided as granules. The size and quantity of granules can be selected to achieve a particular rate of expansion and/or target characteristics of the device 10 in the expanded state. For example, in some embodiments, the size of the granules can define an encapsulated volume within walls 42. As water permeates into these encapsulated volumes the granules can dissolve and the encapsulated volume will expand. The size of the granule is correlated to the concentration of the solute 44 within the encapsulated volume, which will affect the osmotic gradient between the encapsulated volume and its external environment. Thus, smaller granules will generally result in less swelling while larger granules will generally result in more swelling. Similarly, a larger concentration of solute 44 encapsulated within walls 42 will generally result in more swelling while lower concentrations will generally result in less swelling. The solute 44 can include granules within a size range of about 100 to about 500 mesh or about 200 to about 325 mesh. The solute 44 can include biocompatible materials capable of establishing an osmotic gradient, including a salt, such as sodium chloride.

In some embodiments, solute 44 can be an ionic solute selected from the group consisting of sodium, potassium, calcium, chloride, iodide, bromide, carbonate, bicarbonate, sulfate, sulfite, phosphate, acetate, and combinations thereof. In some embodiments, solute 44 can be a water-soluble organic species. Water-soluble organic species include, but are not limited to amino acids, conjugate bases of amino acids, carboxylic acids, conjugate bases of carboxylic acids, (e.g. pyruvate, succinate, etc.), alcohols comprising 2 or more carbon atoms, monomeric and dimeric sugars, and peptides.

According to some embodiments, the granules of solute 44 can be mixed with an elastomer that will be included in the walls 42 of the matrix 40. The elastomer can include one or more biocompatible materials capable of being semipermeable. For example, the elastomer can include silicone. The solute can be mixed with the elastomer at a ratio of about 1% to about 20% by weight, for example about 5% to about 10% by weight. The concentration of solute in the elastomer can be selected to achieve a particular rate of expansion and/or target characteristics of the device 10 in the expanded state. For example, a human body can have solutes in interstitial fluids that include sodium, potassium, calcium, chloride, phosphate, and bicarbonate. In addition, small peptides or glucose can be present. These solutes can be present in a total concentration of about 240 mM to about 272 mM. The concentration of the solute 44 in the elastomer can be configured in order to achieve a final concentration of solute 44 when device 10 is in the expanded state that is similar to that of interstitial fluids in a human body.

According to some embodiments, the mixture is formed into the matrix 40 by a process that creates the chambers 46. For example, the mixture is subjected to an open cell foaming process, such as air entrapment, thermal decomposition with a blowing agent, or porogen bead fusion technology. By further example, the matrix 40 could be molded, 3-D printed, and/or be a two-dimensional mesh that is folded or stacked into 3-D shapes. The elastomer of the mixture is cured and formed approximately into the shape of the matrix 40 that is desired when the device 10 achieves the expanded state. The permeability of the matrix 40 can be programmed or altered based on certain parameters. For example, selections can be made with regard to the composition of the polymer, molecular weight, functional groups, wall thickness, chamber or pore size, and/or surface area of the matrix. The matrix 40 can be shaped during and/or after curing. According to some embodiments, the matrix 40 can be divided or formed into segments 48.

According to some embodiments, the matrix 40 is encased within the shell 20. For example, the shell 20 can be deposited upon the matrix 40 by dip casting in elastomer (e.g., silicone) dispersion. Alternatively or in combination, the shell 20 can be formed independently of the matrix 40, and the matrix 40 can be inserted within the shell 20, such as by separate insertion of individual segments 48.

According to some embodiments, the shell 20 can be provided with the access valve 30. For example, an opening of the shell 20 can be patched with an access valve component. The access valve 30 can provide controlled inflation and/or deflation capabilities.

Figure 7:
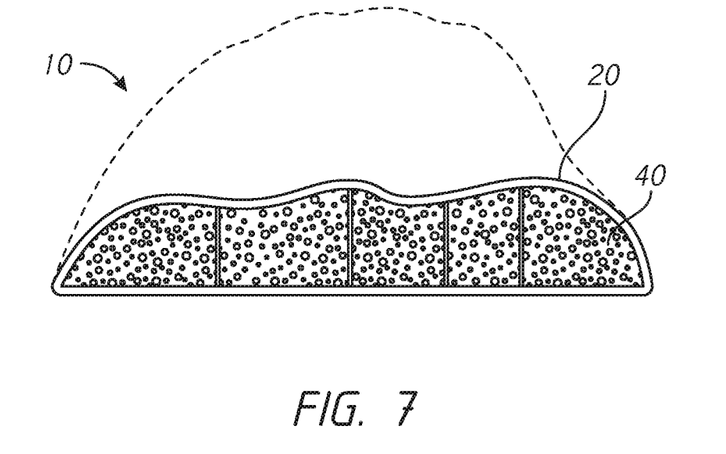
FIG. 7 illustrates a front cross-sectional view through a prosthetic implant in a collapsed state, according to some embodiments of the present disclosure.
Figure 8:
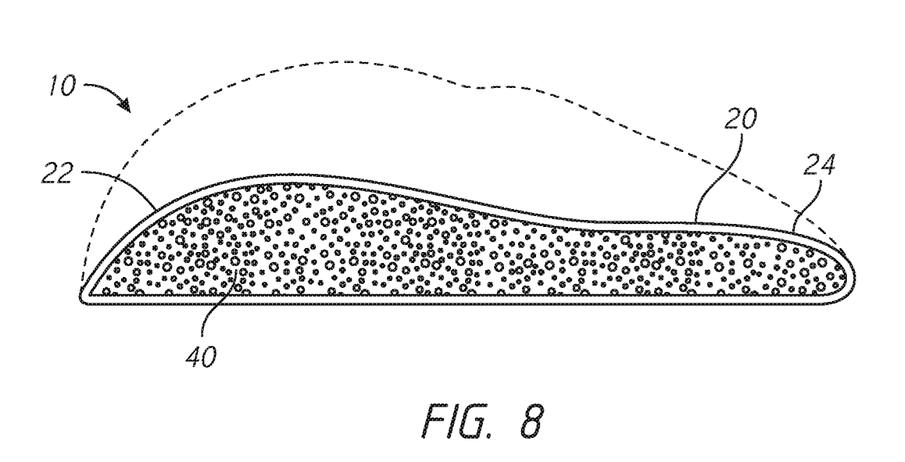
FIG. 8 illustrates a side cross-sectional view through a prosthetic implant in a collapsed state, according to some embodiments of the present disclosure.

According to some embodiments, the device 10 can be collapsed in preparation for implant. For example, a filling tube (not shown) can be connected to the access valve 30 of the device 10. The device 10 can be collapsed, as illustrated in FIGS. 7 and 8, by removing air or other fluids from within the matrix 40 (e.g., from the chambers 46). The collapsed state of the device 10 provides a smaller profile for percutaneous entry into the patient.

According to some embodiments, the device 10 can be inserted into the patient. The device 10 can be implanted in any number of well-known methods. For instance, a number of possible incisions used by surgeons include an inframammary incision, a periareolar incision, and a transaxillary incision. A resilient sizer may be used to determine the size (and possibly shape) of the appropriate implant. While the device 10 is in the collapsed state, the surgeon delivers the implant through the chosen incision.

According to some embodiments, the device 10 can be provided with an amount of a priming solution. For example, a priming solution (e.g., saline) can be provided through the access valve 30 to within the shell 20. The priming solution can be a solution of the solute 44 that is embedded within the walls 42 or different solute. The amount of priming solution can be about 10 cc to about 500 cc, such as about 50 cc to about 100 cc. After implant, any tools, such as a filling tube, within the patient can be removed and the incision can be closed.

The presence of the priming solution can establish an osmotic gradient across the boundary of the device 10. According to some embodiments, the water component from the priming solution will be slowly absorbed through the semi-permeable walls 42 of the matrix 40 and into the many enclosed cells containing granules of the solute 44 in the matrix 40. The absorbed priming solution will gradually increase in solute concentration, thus creating an osmotic gradient between the inside of the device 10 and its external environment, including body tissues. Diffusion of water will then be driven towards absorption within the device 10 through the semi-permeable shell 20. This diffusion of water into the device 10 moves the osmotic gradient towards an osmotic equilibrium with the external environment. As more water is transported into the device 10 (e.g., through the shell 20), the solute 44 embedded in the matrix 40 likewise creates an osmotic gradient between the matrix and its external environment, which drives diffusion of water to absorb into the matrix. This diffusion and absorption will continue causing the device to swell as the osmotic gradient is driven towards reaching an osmotic equilibrium across semi-permeable membranes.

Expansion can be terminated based on characteristics of the device 10. According to some embodiments, expansion can terminate when the solution within the matrix 40 is at equilibrium with the external environment. For example, the expansion can terminate when the solution within the device 10 has a concentration of about 0.9% NaCl. Expansion on this basis can terminate regardless of whether the device 10 has elastic properties that would allow the absorption of additional fluid.

According to some embodiments, expansion can terminate when the device 10 reaches the designed limits of expansion preventing further absorption of water. For example, elastic properties of the matrix 40 and/or the shell 20 can constrain the device 10 by limiting further expansion. As such, the osmotic pressure can reach equilibrium with pressure arising from the elastic properties of the matrix 40 and/or the shell 20. Expansion on this basis can terminate regardless of whether the solution within the device 10 is at osmotic equilibrium with the external environment.

As discussed herein, the rate of expansion of the device can be programmed based on properties of the device 10, such as concentration of solute 44, size and number of the granules of solute 44, permeability of the shell 20, permeability of the matrix 40, elastic properties of the shell 20, and/or elastic properties of the matrix 40. Accordingly, the rate of expansion can be programmed to facilitate adaptation of the device 10 within the body. For example, the rate of expansion can be similar to or slower than a rate of expansion of body tissue during a natural biological process, such as pregnancy. Such a rate of expansion allows the body to adapt to the increasing volume of the device 10 while avoiding tissue damage, scarring, stretch marks, pain, and discomfort.

According to some embodiments, the device 10 can have a rate of expansion in which the device 10 increases its volume by less than or about 10%, 20%, 30%, 40%, 50%, 60%, 70%, 80%, 90%, 100% of the target volume per week. According to some embodiments, the device 10 can have a rate of expansion in which the device 10 increases its volume by less than or about 10 cc per week, 20 cc per week, 30 cc per week, 40 cc per week, 50 cc per week, 60 cc per week, 70 cc per week, 80 cc per week, 90 cc per week, 100 cc per week, 150 cc per week, or 200 cc per week. According to some embodiments, the time between initial implant and achieving the target volume can be less than or about 1 week, 2 weeks, 3 weeks, 4 weeks, 1 month, 2 months, 3 months, 4 months, 5 months, 6 months, or 1 year.

As discussed herein, the target characteristics of the device 10 in the expanded state can be programmed based on properties of the device 10, such as concentration of solute 44, size and number of the granules of solute 44, elastic properties of the shell 20, and/or elastic properties of the matrix 40. For example, expansion can terminate based on the osmotic gradient and/or the elastic limits of the device 10.

According to some embodiments, the device 10 can have a target volume in the expanded state that is greater than or equal to about 100% of the volume in the collapsed state, 200% of the volume in the collapsed state, 300% of the volume in the collapsed state, 400% of the volume in the collapsed state, or 500% of the volume in the collapsed state. According to some embodiments, the device 10 can have a target volume in the expanded state that is greater than or equal to about 20 cc, 30 cc, 40 cc, 50 cc, 60 cc, 70 cc, 80 cc, 90 cc, 100 cc, 200 cc, 300 cc, 400 cc, 500 cc, 600 cc, 700 cc, 800 cc, 900 cc, 1,000 cc, 1,200 cc, 1,400 cc, 1,600 cc, 1,800 cc, or 2,000 cc.

According to some embodiments, if the volume and shape of the device meet the patient's needs, the device 10 can remain in place as a permanent implant. Thus, the device 10 can perform its roles as tissue expander and permanent implant with only one procedure.

The device 10 can be accessed if needed for removal, maintenance, or any other purpose. According to some embodiments, the device 10 can be accessed through a small incision. The fluid volume within the device 10 can be increased or decreased, for example through the access valve 30. In some embodiments, the device 10 can be accessed for fluid volume adjustment percutaneously with a needle.

According to some embodiments, the device 10 can be deflated and removed. For example, the device 10 can be accessed through a small incision. The shell 20 can be pierced to access the matrix 40. The device 10 can be collapsed by expelling fluid from within the device 10. While in the collapsed state, the device 10 can be removed from the patient. According to some embodiments, the matrix 40 can be removed from the shell 20 prior to removal of the entire device 10 from the patient. For example, segments 48 can be separately removed from the shell 20 through the small incision. The size of the individual segments 48 facilitates removal through smaller working spaces than would be required for simultaneous removal of the entire device 10.

Illustration of Subject Technology as Clauses

Various examples of aspects of the disclosure are described as numbered clauses (1, 2, 3, etc.) for convenience. These are provided as examples, and do not limit the subject technology. Identifications of the figures and reference numbers are provided below merely as examples and for illustrative purposes, and the clauses are not limited by those identifications.

Clause 1. A device for implanting into a body of a living subject, the device comprising an expandable elastomeric matrix and granules of a solute embedded within the matrix, wherein the matrix defines boundaries of a plurality of chambers within the matrix, wherein the boundaries are permeable to water at a temperature of between 35° C. and 41° C.

Clause 2. The device of Clause 1, wherein the boundaries are impermeable to an ionic solute selected from the group consisting of sodium, potassium, calcium, chloride, iodide, bromide, carbonate, bicarbonate, sulfate, sulfite, phosphate, acetate, and combinations thereof.

Clause 3. The device of Clause 1 or Clause 2, wherein the boundaries are impermeable to a water-soluble organic species.

Clause 4. The device of Clause 3, wherein the water-soluble organic species is selected from the group consisting of amino acids, conjugate bases of amino acids, carboxylic acids, conjugate bases of carboxylic acids, alcohols comprising 2 or more carbon atoms, monomeric and dimeric sugars, peptides, and combinations thereof.

Clause 5. The device of any one of Clauses 1-4, wherein the granules of solute have an average particle size in the range of about 100 to about 500 mesh.

Clause 6. The device of any one of Clauses 1 to 5, further comprising a shell extending about a periphery of the matrix to enclose the matrix therewithin.

Clause 7. The device of Clause 6, wherein the shell is permeable to water at a temperature of between 35° C. and 41° C.

Clause 8. The device of Clause 6 or Clause 7, wherein the shell is impermeable to an ionic solute selected from the group consisting of sodium, potassium, calcium, chloride, iodide, bromide, carbonate, bicarbonate, sulfate, sulfite, phosphate, acetate, and combinations thereof.

Clause 9. The device of any one of Clauses 6 to 8, wherein the shell is impermeable to a water-soluble organic species.

Clause 10. The device of Clause 9, wherein the water-soluble organic species is selected from the group consisting of amino acids, conjugate bases of amino acids, carboxylic acids, conjugate bases of carboxylic acids, alcohols comprising 2 or more carbon atoms, monomeric and dimeric sugars, peptides, and combinations thereof.

Clause 11. The device of any one of Clauses 6 to 10, further comprising a priming solution within the shell, the priming solution having a concentration of a solute.

Clause 12. The device of Clause 11, wherein the solute of the priming solution and the granules of solute embedded within the matrix are comprised of the same material.

Clause 13. The device of Clause 11, wherein the solute of the priming solution and the granules of solute embedded within the matrix are comprised of different materials.

Clause 14. The device of Clause 11, wherein the priming solution comprises saline.

Clause 15. The device of any one of Clauses 6 to 14, wherein the shell has a first portion and a second portion that each have expansion ratios of expanded volume to pre-expansion volume, the expansion ratio of the second portion being greater than the expansion ratio of the first portion.

Clause 16. The device of any one of Clauses 6 to 15, wherein the matrix comprises a plurality of segments within the shell.

Clause 17. The device of Clause 16, wherein at least two of the segments have different rates of expansion.

Clause 18. The device of any one of Clauses 6 to 17, wherein the matrix has a maximum potential volume of expansion, and the shell restricts the matrix from expanding to the maximum potential volume of expansion.

Clause 19. The device of any one of Clauses 1 to 18, wherein the expandable matrix comprises a foamed elastomer.

Clause 20. The device of any one of Clauses 1 to 19, wherein the elastomeric matrix comprises silicone.

Clause 21. The device of any one of Clauses 1 to 20, wherein the granules of solute comprise sodium chloride.

Clause 22. The device of any one of Clauses 1 to 21, wherein the chambers are fluidly interconnected as open cells of the matrix.

Clause 23. The device of any one of Clauses 1 to 22, further comprising an access valve in fluid communication with the plurality of chambers.

Clause 24. The device of any one of Clauses 1 to 23, wherein when exposed to an external fluid, an osmotic gradient is created across a boundary of the device to facilitate fluid permeation and expansion of the chambers until an osmolarity of fluid within the chambers is equal to an osmolality of the external fluid.

Clause 25. The device of any one of Clauses 1 to 24, wherein the boundaries are permeable to water at a temperature lower than about between 41° C.

Clause 26. A method of implanting an expandable device, the method comprising: implanting the device, in a collapsed state, within a living subject, wherein the device comprises an expandable elastomeric matrix and granules of a solute embedded within the matrix, wherein the matrix defines boundaries of a plurality of chambers within the matrix; and permitting the device to be exposed to fluid within the living subject to create an osmotic gradient across a boundary of the device, whereby the fluid permeates the elastomer and expands the chambers.

Clause 27. The method of Clause 26, wherein the elastomer comprises a fluid permeation profile whereby fluid permeation occurs at a rate to permit device expansion of not more than 100% within 1 week.

Clause 28. The method of Clause 26 or 27, further comprising puncturing the matrix to expose the plurality of chambers to an external environment.

Clause 29. The method of any one of Clauses 26 to 28, further comprising removing the device from the living subject by cutting the matrix to segment the device.

Clause 30. The method of any one of Clauses 26 to 29, wherein the device further comprises an access valve in fluid communication with the plurality of chambers, and wherein the method further comprises: connecting a filling tube to the access valve; collapsing the matrix by removing air within the plurality of chambers; and after the implanting, injecting a priming solution into the plurality of chambers.

Clause 31. The method of any one of Clauses 26 to 30, wherein the permitting the device to be exposed to fluid further comprises permitting the fluid to expand the chambers until an osmolarity of fluid within the chambers is equal to an osmolarity of fluid in the living subject, wherein the fluid in the living subject is in fluid communication with the device and is external to the device.

Clause 32. The method of any one of Clauses 26 to 31, wherein the device further comprises a shell extending about a periphery of the matrix, and wherein fluid expands the chambers until further expansion is prevented by the shell.

Clause 33. A method of manufacturing an expandable implant device, the method comprising: mixing granules of a solute with an elastomer; forming a matrix with the elastomer and granules embedded within the elastomer, the elastomer defining boundaries of a plurality of chambers within the matrix; and curing the elastomer, such that the boundaries of the matrix are permeable to water at a temperature of between 35° C. and 41° C.

Clause 34. The method of Clause 33, further comprising placing a shell about a periphery of the matrix.

Clause 35. The method of Clause 34, further comprising: placing an access valve across the shell and in fluid communication with the chambers.

Clause 36. The method of any one of Clauses 33 to 35, wherein the forming comprises forming the chambers as interconnected open cells in the matrix.

Clause 37. The method of any one of Clauses 33 to 36, wherein the device further comprises an access valve in fluid communication with the plurality of chambers, and wherein the method further comprises: connecting a tube to the access valve; and collapsing the matrix by removing air from within the plurality of chambers.

Further Considerations

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

A phrase such as "an aspect" does not imply that such aspect is essential to the subject technology or that such aspect applies to all configurations of the subject technology. A disclosure relating to an aspect may apply to all configurations, or one or more configurations. An aspect may provide one or more examples of the disclosure. A phrase such as "an aspect" may refer to one or more aspects and vice versa. A phrase such as "an embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples of the disclosure. A phrase such "an embodiment" may refer to one or more embodiments and vice versa. A phrase such as "a configuration" does not imply that such configuration is essential to the subject technology or that such configuration applies to all configurations of the subject technology. A disclosure relating to a configuration may apply to all configurations, or one or more configurations. A configuration may provide one or more examples of the disclosure. A phrase such as "a configuration" may refer to one or more configurations and vice versa.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While certain aspects and embodiments of the subject technology have been described, these have been presented by way of example only, and are not intended to limit the scope of the subject technology. Indeed, the novel methods and systems described herein may be embodied in a variety of other forms without departing from the spirit thereof. The accompanying claims and their equivalents are intended to cover such forms or modifications as would fall within the scope and spirit of the subject technology.

What is claimed is:

1. A tissue expander device for implanting into a body of a living subject, the device comprising:
    an expandable elastomeric matrix and granules of a solute embedded within the matrix, wherein the matrix defines boundaries of a plurality of chambers within the matrix, wherein the boundaries are permeable to water at a temperature of between 35° C. and 41° C.; and
    a shell extending about a periphery of the matrix to enclose the matrix therewithin.

2. The device of claim 1, wherein the shell is permeable to water at a temperature of between 35° C. and 41° C.

3. The device of claim 1, further comprising a priming solution within the shell, the priming solution having a concentration of a solute.

4. The device of claim 1, wherein the shell has a first portion and a second portion that each have expansion ratios of expanded volume to pre-expansion volume, the expansion ratio of the second portion being greater than the expansion ratio of the first portion.

5. The device of claim 1, wherein the matrix comprises a plurality of segments within the shell.

6. The device of claim 5, wherein at least two of the segments have different rates of expansion.

7. The device of claim 1, wherein the matrix has a maximum potential volume of expansion, and the shell restricts the matrix from expanding to the maximum potential volume of expansion.

8. The device of claim 1, wherein the expandable elastomeric matrix comprises a foamed elastomer.

9. The device of claim 1, wherein the expandable elastomeric matrix comprises silicone.

10. The device of claim 1, wherein the granules of solute comprise sodium chloride.

11. The device of claim 1, wherein the chambers are fluidly interconnected as open cells of the matrix.

12. The device of claim 1, further comprising an access valve in fluid communication with the plurality of chambers.

13. The device of claim 1, wherein when exposed to an external fluid, an osmotic gradient is created across a boundary of the device to facilitate fluid permeation and expansion of the chambers until an osmolarity of fluid within the chambers is equal to an osmolarity of the external fluid.

14. A method of implanting an expandable tissue expander device, the method comprising:
   implanting the device, in a collapsed state, within a living subject, wherein the device comprises:
      an expandable elastomeric matrix and granules of a solute embedded within the matrix, wherein the matrix defines boundaries of a plurality of chambers within the matrix, and;
      a shell extending about a periphery of the matrix to enclose the matrix therewithin; and
   permitting the device to be exposed to fluid within the living subject to create an osmotic gradient across a boundary of the device, whereby the fluid permeates the elastomer and expands the chambers.

15. The method of claim 14, wherein the elastomer comprises a fluid permeation profile whereby fluid permeation occurs at a rate to permit device expansion of not more than 100% within 1 week.

16. The method of claim 14, wherein the device further comprises an access valve in fluid communication with the plurality of chambers, and wherein the method further comprises:
   connecting a filling tube to the access valve;
   collapsing the matrix by removing air within the plurality of chambers; and
   after the implanting, injecting a priming solution into the plurality of chambers.

17. The method of claim 14, wherein the permitting the device to be exposed to fluid further comprises permitting the fluid to expand the chambers until an osmolarity of fluid within the chambers is equal to an osmolarity of a fluid in the living subject, wherein the fluid in the living subject is in fluid communication with the device and is external to the device.

18. The method of claim 14, wherein the device further comprises a shell extending about a periphery of the matrix, and wherein fluid expands the chambers until further expansion is prevented by the shell.

* * * * *